United States Patent [19]

Higgins

[11] Patent Number: 4,875,481

[45] Date of Patent: Oct. 24, 1989

[54] CATHETER WITH COILED WIRE ATTACHMENT

[75] Inventor: Sheryl W. Higgins, Plantation, Fla.

[73] Assignee: Cordis Corporation, Miami Lakes, Fla.

[21] Appl. No.: 214,171

[22] Filed: Jul. 1, 1988

[51] Int. Cl.⁴ ............................................. A61M 29/02
[52] U.S. Cl. .................................. 128/344; 128/348.1; 604/96
[58] Field of Search ...................... 128/344, 348.1, 656, 128/657, 772; 604/96

[56] References Cited

U.S. PATENT DOCUMENTS 4,614,188 9/1986 Bazell et al. ...................... 128/348.1
4,723,936 2/1988 Buchbinder et al. .............. 604/96 X
4,787,399 11/1988 Bonello et al. ......................... 604/96

Primary Examiner—Michael H. Thaler
Attorney, Agent, or Firm—Gerstman & Ellis, LTD.

[57] ABSTRACT

A catheter such as a medical catheter for PTCA procedures or the like. The catheter has a longitudinally extending wire therein, typically a steering wire. A catheter hub is positioned on the proximal end of the catheter. By this invention, the wire defines a coiled end positioned within a bore of the catheter hub and secured to the hub. Thus, fluids can flow through the bore of the hub and coiled wire end to and from the catheter, for example for the purpose of inflating or deflating a catheter balloon. At the same time, the same hub can be used to steer the distal end of the catheter by rotation of the hub in a conventional catheter steering technique.

13 Claims, 1 Drawing Sheet

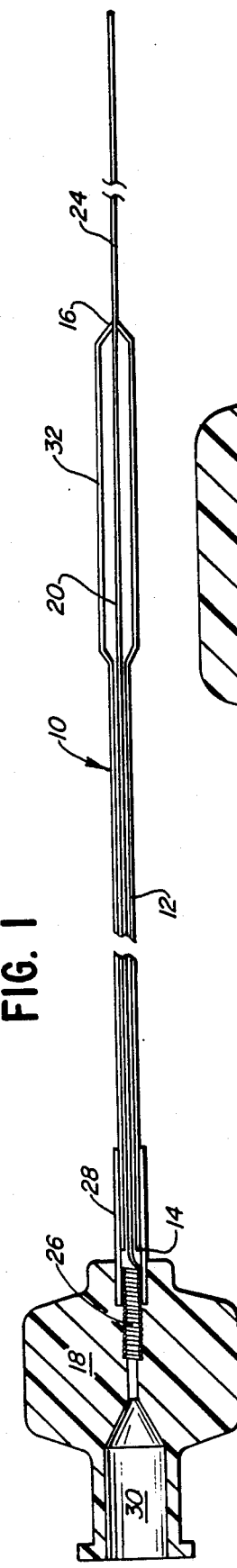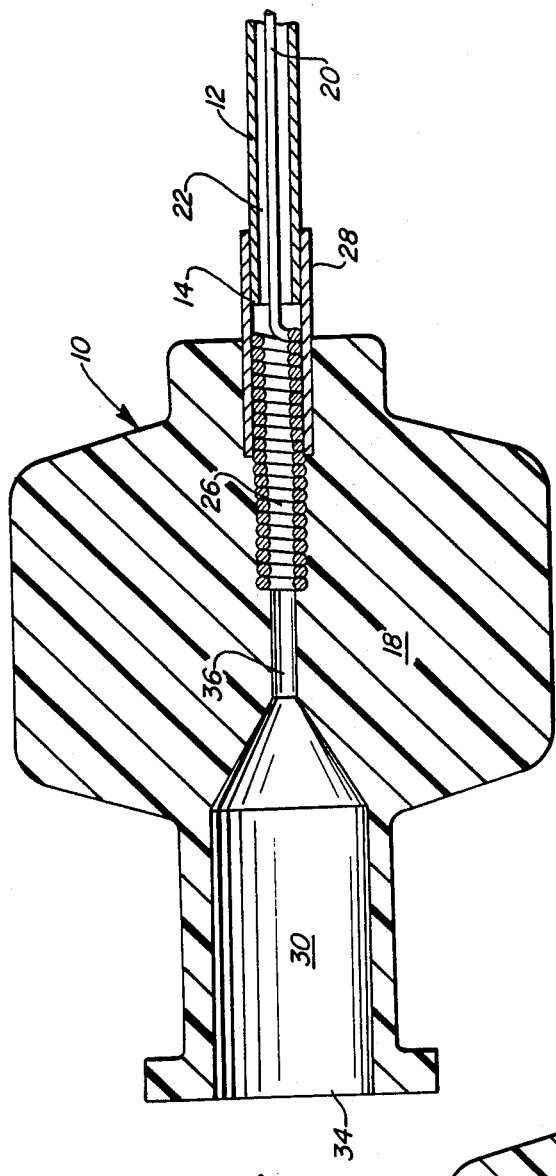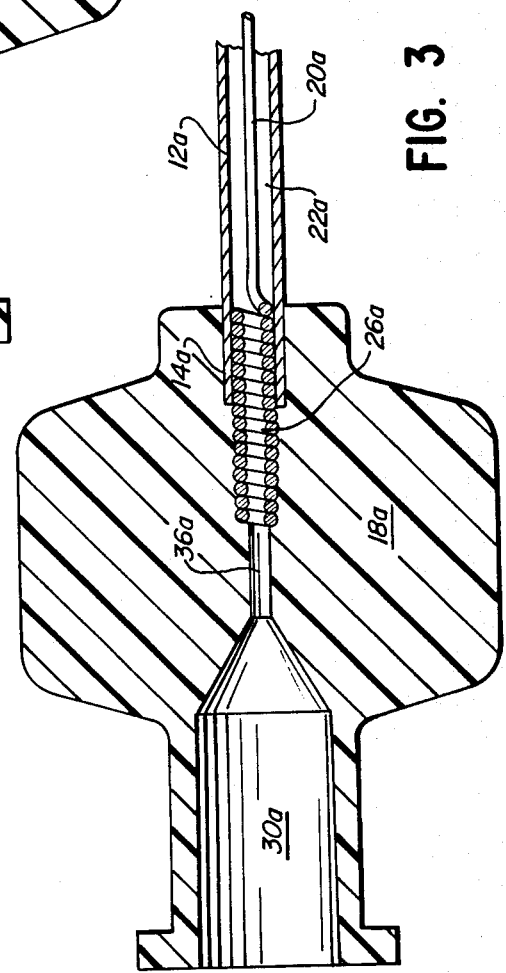

CATHETER WITH COILED WIRE ATTACHMENT

BACKGROUND OF THE INVENTION

Catheters for medical procedures such as the well known PTCA procedure are desirably rotatable at their distal ends while positioned within the blood vessel of a patient. This may be accomplished by providing to the catheter a longitudinally positioned steering wire, which facilitates steering of the catheter by stiffening it rotationally so that rotation of the proximal end of the catheter will cause rotation of the distal end as well. Then, if the distal end of the catheter has a curve in it, rotation of the catheter can cause the curved end to rotate as well, to assist in directing the catheter into the proper blood vessel when a blood vessel junction is encountered, or the like.

Typically, blood vessel catheters of the prior art carry a hub at their proximal end, and also a branched connection along the length of the catheter which terminates in a second hub. For example, in a PTCA catheter, one of the hubs may be used to secure the longitudinal steering wire which permits rotation of the distal end of the catheter when emplaced in the blood vessel. The other hub carries a port which communicates with an inflation balloon in the catheter. In the case of a PTCA catheter, this is for dilating sclerotic lesions in arteries after the catheter has been properly emplaced.

In accordance with this invention, a simplified, effective catheter is provided, primarily for medical purposes such as PTCA, in which a single hub may provide the combined functions of proximal mounting for a steering wire, plus a connection site for an inflation lumen which communicates with a balloon in the catheter. The connection site of the inflation lumen may be, for example, a simple luer-type connection through which a syringe may inject an inflation fluid to inflate the balloon, for example a 50/50 mixture of X-ray contrast media and saline solution. Thus, the catheter of this invention is substantially simplified from prior art catheters of equivalent function, having one hub rather than two hubs plus a branched connection. Nevertheless, the catheter may exhibit excellent steerable qualities by means of the longitudinal wire carried therein, while also carrying an inflation balloon.

The catheter of this invention exhibits a novel connection between the longitudinal steering wire carried therein and the hub to which it is attached, to accomplish the purposes of this invention.

DESCRIPTION OF THE INVENTION

In this invention, a catheter is provided having a longitudinally extending wire therein and a catheter hub positioned on the proximal end of the catheter. In accordance with this invention, the hub defines a bore, while the wire defines a coiled end positioned within the bore, and secured to the hub. As a result of this, fluids can flow through the bore and coiled wire end to and from the catheter. This, in turn, permits the double use of the hub as an anchoring site as described above for the wire, which is typically a relatively stiff catheter steering wire, and as a connection site to the inflation lumen of the catheter.

If desired, the hub may carry a tubular strain relief member, with a portion of the catheter and wire being positioned within the tubular strain relief member. A portion of the wire coil may be bonded to the hub within the bore, while a portion of the coil may occupy the tubular strain relief member.

Alternatively, the hub may be molded about at least a portion of the coil, with a typically conventional insert-type injection molding procedure being used so that at least outer portions of the coil are embedded in the hot plastic of the newly molded hub during the molding process, to provide a strong connection between the coiled end of the catheter wire and the hub. The area within the coiled wire and the bore defined through the hub may be produced by the use of a conventionally tapered core pin during the molding operation, the tapered core pin tapering, for example, from a diameter of 0.021 to 0.018 inch, so that it is easily removed from the mold upon opening.

Accordingly, the hub as produced by this invention can serve both for providing fluid connection to the catheter interior, typically for balloon inflation, as well as for rotationally steering the catheter with the attached, coiled-end wire, so that the catheter can be free of any other hub if desired. However, it is contemplated that, if desired for added functions, other catheter hubs and branched connections may be added to the catheter of this invention. Thus, the catheter of this invention may carry a balloon which is inflatable by fluid passing through the hub.

DESCRIPTION OF THE DRAWINGS

FIG. 1 is a longitudinal sectional view of a medical catheter made in accordance with this invention;

FIG. 2 is an enlarged, fragmentary, sectional view of a portion of FIG. 1; and

FIG. 3 is an enlarged, fragmentary, sectional view similar to FIG. 2 of a different embodiment of the catheter of this invention, which otherwise is similar to the embodiment shown in FIG. 1;

DESCRIPTION OF SPECIFIC EMBODIMENTS

Referring to FIGS. 1 and 2, a catheter for the medical PTCA procedure is disclosed. This procedure is a well-known and extensively used medical procedure for dilating arteriosclerotic lesions in arteries of the patient, being typically a procedure which is performed in lieu of a coronary bypass operation, and which is generally deemed to be a significantly less severe procedure than coronary bypass surgery. By expansion of the catheter balloon, the arteriosclerotic lesion is crushed outwardly, to at least temporarily open up the artery in question to provide the patient with a better blood supply.

Catheter 10 is disclosed, being of generally conventional manufacture except as otherwise disclosed herein. As is conventional, catheter 10 defines a catheter body 12 having a proximal end 14 and a distal end 16, and a catheter hub 18 which is typically made of molded plastic, carried at proximal end 14 of catheter body 12.

As shown, a catheter steering or guide wire 20 is carried within the lumen 22 of catheter 12, extending substantially the length thereof and defining a projecting wire portion 24 beyond the distal end 16 of catheter body 12, in the conventional manner of a rotationally steerable PTCA catheter. The distal portion of catheter 10 may be curved if desired, or, as shown herein, may be straight. In either circumstance, the rotation capability provided by wire 20 enhances the steerability of the distal portion of catheter 10 for guiding it into the proper blood vessel during catheter advancement when vessel intersections are encountered.

In accordance with this invention, catheter guide wire 20 terminates at its proximal end in a helical coil 26, preferably a generally tight helical coil as shown where the individual coiled loops are substantially not spaced from each other. In the embodiment shown in FIGS. 1 and 2, a tubular strain relief member 28 is provided, to which the proximal end 14 of catheter body 12 may be secured by an appropriate adhesive or the like. A portion of coil 26 is tightly secured within tubular strain relief 28 as shown. Strain relief 28 and coil 26, in the process of manufacturing and attaching of hub 18, may be placed into an appropriate jig, with the plastic hub 18 being insert molded into position about coil 26 and tubular strain relief 28, to provide firm, strong bonding of the members together, both adhesively and mechanically. Specifically, the melted molding compound can penetrate in small amounts between the coils of wire coil 26, and can also enter into intimate, bonding and adhering contact with strain relief tube 28, to accomplish this purpose.

Thus, after attachment of hub 18 onto catheter body 12 by means of its attachment with coil 26 and strain relief member 28, bore 30 provides communication to the interior of catheter body 12 from the exterior, with fluid being capable of flowing through the interior of coil 26 and strain relief tube 28 to enter catheter lumen 22. Catheter lumen 22, in turn, communicates with the interior of enlarged catheter balloon portion 32, so that balloon 32 may be easily inflated, after catheter 10 is emplaced in the arterial system of a patient, by connection of a syringe or the like with the proximal end 34 of bore 30. Bore portion 36 may be slightly tapered inwardly from its proximal end to its distal end, in a shape complimentary to the shape of the tapered core pin as described above, for ease of removal of the core pin after insert molding of hub 18.

Thus, a catheter in accordance with this invention is provided in which a single hub 18 serves a double function. It serves as the anchor and connection for catheter steering wire 20 through the connection of hub 18 and coiled wire section 26, which is secured to hub 18. Additionally, a connecting bore 30 is provided through hub 18, for connection with catheter lumen 22, typically for inflation of balloon 32 in a manner that is otherwise conventional except for the distinctions of catheter structure described herein.

Turning to FIG. 3, an alternate embodiment is disclosed. In this embodiment, catheter body 12a, which carries steering wire 20a in a manner similar to that of the previous embodiment, has its proximal end 14a directly connected to catheter hub 18a. Steering wire 20a terminates at its proximal end in a helical coil 26a, as in the previous embodiment, which, along with catheter 12a, is bonded to hub 18a. The technique of bonding may be a similar insert molding technique as in the previous embodiment, or conventional adhesives or the like may be used as an alternate or supplement to the previously described bonding technique.

As before, catheter hub 18a defines a bore 30a with inner portion 36a of bore 30a communicating through wire coil 26a to the lumen 22a of catheter portion 12a.

Thus the catheter of FIG. 3 may function in a manner which is similar or identical to the catheter of FIGS. 1 and 2, in which rotation by manipulation of hub 18a results in rotation of the distal end of the catheter, through the action of catheter steering wire 20a. Also, inflation fluids or other fluids may be passed through hub bore 30a into or out of catheter lumen 22a for inflation of a balloon or for any other desired purpose.

The above has been offered for illustrative purposes only, and is not intended to limit the scope of the invention of this application, which is defined in the claims below.

That which is claimed is:

1. In a catheter having a longitudinally extending steering wire therein and a catheter hub positioned on an end of said catheter, the improvement comprising, in combination:

said hub defining a bore, said wire defining a generally straight portion comprising most of the length of said wire and a coiled end unitary with said straight portion and positioned within said bore and secured to said hub, whereby fluids can flow through said bore and coiled wire end to and from said catheter.

2. The catheter of claim 1 in which said hub carries a tubular strain relief member, a portion of the catheter and wire being positioned within said tubular strain relief member.

3. The catheter of claim 2 in which a portion of said coiled end is bonded to said hub within said bore, and a portion of said coiled end occupies said tubular strain relief member.

4. The catheter of claim 1 in which said hub is molded about at least a portion of said coiled end.

5. The catheter of claim 1 in which said hub serves both for providing fluid connection to the interior of the catheter and for steering the catheter with said wire, said catheter being free of any other hub.

6. The catheter of claim 5 which carries a balloon which is inflatable by fluid passing through said hub.

7. In a catheter having a longitudinally extending steering wire therein and a catheter hub positioned on the proximal end of said catheter, said catheter defining an inflatable balloon member positioned adjacent the distal end of said catheter, the improvement comprising, in combination:

said hub defining a bore, said wire defining a generally straight portion comprising most of the length of said wire and a coiled end unitary with said straight portion and positioned within said bore and secured in said hub, whereby fluids can flow through said bore and coiled wire end to and from said catheter to inflate and deflate the balloon of said catheter, said hub serving both for providing said fluid connection for inflating and deflating the catheter balloon and for steering the catheter with said wire, said catheter being free of any other hub.

8. The catheter of claim 7 in which said hub carries a tubular strain relief member, a portion of the catheter and steering wire being positioned within said tubular strain relief member.

9. The catheter of claim 8 in which a portion of said coiled end is bonded to said hub within said bore, and a portion of said coiled end occupies said tubular strain relief member.

10. The catheter of claim 7 in which said hub is molded about at least a portion of said coiled end.

11. The catheter of claim 7 which defines a catheter body, said catheter body being directly bonded to said hub.

12. In a catheter having a longitudinally extending steering wire therein and a catheter hub positioned on an end of said catheter, the improvement comprising, in combination:

said hub defining a bore, said wire defining a generally straight portion comprising a substantial portion of the length of said wire and a coiled end unitary with said straight portion and positioned within said bore, said hub defining a plastic member which has been insert molded into position about said coiled end for securance of said hub and wire together, whereby fluids can flow through said bore and coiled wire end to and from said catheter.

13. The catheter of claim 12 which carries a balloon inflatable by fluid passing through said hub.

* * * * *